United States Patent
Zhang et al.

(10) Patent No.: US 11,304,754 B2
(45) Date of Patent: Apr. 19, 2022

(54) CIRCULAR MICROWAVE ABLATION ANTENNA AND SYSTEM

(71) Applicant: Mima-Pro (Nan Tong) Scientific Inc, Nantong (CN)

(72) Inventors: Peng Zhang, Nantong (CN); Ting Yang, Nantong (CN)

(73) Assignee: Mima-Pro (Nan Tong) Scientific Inc, Nantong (CN)

(*) Notice: Subject to any disclaimer, the term of this patent is extended or adjusted under 35 U.S.C. 154(b) by 686 days.

(21) Appl. No.: 16/087,098

(22) PCT Filed: Mar. 14, 2018

(86) PCT No.: PCT/CN2018/078952
§ 371 (c)(1),
(2) Date: Sep. 21, 2018

(87) PCT Pub. No.: WO2018/192325
PCT Pub. Date: Oct. 25, 2018

(65) Prior Publication Data
US 2021/0220048 A1 Jul. 22, 2021

(30) Foreign Application Priority Data
Apr. 20, 2017 (CN) .......................... 201710260121.3

(51) Int. Cl.
*A61B 18/18* (2006.01)
*A61B 18/08* (2006.01)
(Continued)

(52) U.S. Cl.
CPC ........ *A61B 18/1815* (2013.01); *A61B 18/082* (2013.01); *A61B 18/148* (2013.01);
(Continued)

(58) Field of Classification Search
CPC .............. A61B 18/1815; A61B 18/082; A61B 2018/1425; A61B 18/18; A61B 18/1482;
(Continued)

(56) References Cited

U.S. PATENT DOCUMENTS

2009/0187180 A1* 7/2009 Brannan ................. A61B 18/18
606/33
2009/0295674 A1* 12/2009 Bonn ................. A61B 18/1815
343/872

(Continued)

*Primary Examiner* — Linda C Dvorak
*Assistant Examiner* — Lindsay Regan Lancaster
(74) *Attorney, Agent, or Firm* — Bayramoglu Law Offices LLC

(57) ABSTRACT

A circular microwave ablation antenna is provided with a chamber for accommodating the coaxial cable and the conduit, the chamber and the conduit extend forward to the front end of the antenna. An emission window of the antenna is at least partially located in the conduit to enable the cooling medium to cool the emission window area of the antenna. The conduit of the microwave emission area is made of an insulation material, so that the microwave can radiate outward, and the rest of the conduit is made of a microwave shielding material. The choke ring located at the rear side of emission area is hermetically fixed to the conduit, so that the choke ring acts to block the microwave. A gap exists between the choke ring and the needle bar, and the gap is used for the backflow of the cooling medium.

12 Claims, 1 Drawing Sheet

(51) Int. Cl.
    *A61B 18/14*    (2006.01)
    *A61B 18/00*    (2006.01)
(52) U.S. Cl.
    CPC ....... *A61B 18/1477* (2013.01); *A61B 18/1482* (2013.01); *A61B 18/18* (2013.01); *A61B 2018/00023* (2013.01); *A61B 2018/00577* (2013.01); *A61B 2018/00589* (2013.01); *A61B 2018/1425* (2013.01); *A61B 2018/1427* (2013.01); *A61B 2018/1497* (2013.01); *A61B 2018/1861* (2013.01); *A61B 2018/1869* (2013.01); *A61B 2018/1884* (2013.01); *A61B 2018/1892* (2013.01)
(58) Field of Classification Search
    CPC ........ A61B 2018/1427; A61B 18/1477; A61B 18/148; A61B 2018/1892; A61B 2018/00589; A61B 2018/1884; A61B 2018/1497; A61B 2018/1861; A61B 2018/1869; A61B 2018/00023; A61B 2018/00577

See application file for complete search history.

(56)    References Cited

U.S. PATENT DOCUMENTS

2010/0045559 A1*  2/2010  Rossetto ................ H01Q 5/357
                                                    343/792
    2010/0305559 A1* 12/2010  Brannan ................ A61B 18/18
                                                    606/33
    2012/0172863 A1*  7/2012  Brannan ............ A61B 18/1815
                                                    606/33
    2012/0310228 A1* 12/2012  Bonn ................. A61B 18/1815
                                                    606/33

* cited by examiner

CIRCULAR MICROWAVE ABLATION ANTENNA AND SYSTEM

CROSS REFERENCE TO RELATED APPLICATIONS

This application is the national phase entry of International Application PCT/CN2018/078952, filed on Mar. 14, 2018, which is based upon and claims priority to Chinese Patent Application No. 201710260121.3, filed on Apr. 20, 2017, the entire contents of which are incorporated herein by reference.

TECHNICAL FIELD

The present invention relates to a circular microwave ablation antenna, belonging to the technical field of microwave ablation needle.

BACKGROUND

With the progress of modern science and oncology, in the past ten years, breakthroughs have been made in domestic microwave tumor ablation technology. Microwave tumor ablation uses microwave energy to produce a thermal effect when it acts on tissues. In a few minutes to ten minutes, the temperature of the center of the thermal field can reach above 100° C., and the tumor tissue is coagulated and inactivated at an instant high temperature to achieve the treating purpose of tumor ablation. Microwave tumor ablation enables a microwave ablation needle to intervene human tissue lesions, and the front end of the microwave ablation needle to emit microwave energy continuously to perform surgery. Due to its high efficiency, small wound, and controllability for the working depth and range on tissues, microwave tumor ablation is suitable for ablation surgery for whole-body solid tumors.

Currently, the microwave ablation needle used in clinical practice has the following deficiencies:

1. Working temperature is high on the front end of the needle body, which affects the stability of microwave energy emission. Meanwhile, the high temperature of the needle bar will burn normal tissue.

2. Defects exist in the microwave emission structure at the front end of the needle body, which limits the available microwave output power.

3. The current microwave ablation damage shape is not round (long or elliptical), the circularity is less than 0.7, the ablation short diameter is less than 3 cm, thereby being unable to treat a tumor having a size of 3 cm with a needle. Clinical use is greatly limited, and complete ablation therapy cannot be guaranteed, and the results become unpredictable.

In order to solve the above technical problems, applicant submitted a patent application CN201020520138.1 to the Patent Office in September, 2010. The patent application relates to a "water-cooled microwave ablation needle for high-power use", a choke ring (water plugging shaft) is welded on the coaxial cable at the rear side of the transmitting end, a front end of a conduit sleeved outside the coaxial cable is fixed to the choke ring to form an inlet and outlet channel, and the front end (the rear end of the microwave emission region) of the needle body is water-cooled by a cooling medium (water). Thereby, the above problems have been solved to a certain extent. However, the circularity of the solution has not yet reached 0.9. Therefore, further research, development and improvement are still needed.

After the rapid solidification and dehydration of tumor tissue during microwave ablation, the dielectric constant of the tissue changes dynamically, and the dielectric coefficient of core tissue carbonized (140° C.) or coked (about 110° C.) caused by high temperature changes greatly. The wavelength of the microwave will become longer, causing the diffraction ability of the creeping wave to become stronger (the choke ring can be bypassed). At the same time, the carbonized tissue forms a reflecting surface, reflecting some microwave energy to the needle bar direction (the rear end of the antenna). The common result is that the shape of the microwave antenna ablation is not round when the continuous ablation occurs, and the circularity coefficient (short diameter/long diameter) in clinical practice is difficult to exceed 0.7.

SUMMARY

The technical problem to be solved by the present invention is to overcome the above-mentioned disadvantages in the prior art and provide a circular microwave ablation antenna and system.

In order to solve the above technical problem, a circular microwave ablation antenna provided by the present invention includes a needle head, a needle bar, a coaxial cable, a conduit and a choke ring. The antenna is provided with a chamber for accommodating the coaxial cable and the conduit, and a water inlet channel is disposed between the conduit and the coaxial cable, and a water return channel is disposed between the conduit and the needle bar. The chamber and the conduit extend forward to a front end of the antenna, and an emission window of the antenna is at least partially located in the conduit to enable the cooling medium to cool the emission window area of the antenna. The conduit of the microwave emission area is made of a microwave permeable material, so that the microwave can radiate outward, and the rest of the conduit is made of a microwave shielding material. The choke ring located at the rear side of emission area is hermetically fixed to the conduit, so that the choke ring acts to block the microwave, and a gap exists between the choke ring and the needle bar, and the gap is used for the backflow of the cooling medium.

The microwave permeable material is an isolation material, the microwave shielding material is a metal material.

The present invention changes the water-cooling structure of the traditional ablation antenna, and arranges the emission window of the antenna in the conduit, so that the cooling medium (water) can cool the front end of the antenna, preventing the tumor tissue in the high temperature region from being carbonized or coked in a short time. The change of the dielectric coefficient of the tumor tissue in the high temperature region is small, which makes the microwave wavelength basically stable during the surgery, and the climbing ability thereof is weak, and the suppression can be achieved by cooperating with the choke ring. At the same time, the "reflecting surface formed by carbonized tissue" mentioned in the background does not exist, which ensures that the shape of the microwave ablation is round, and the "circularity" coefficient (short diameter/long diameter) reaches 0.95. Moreover, because the temperature of the high temperature region of the needle head is effectively controlled, it is possible to realize a larger ablation radius (5 cm or more) by increasing the power and the ablation time.

In addition, the present invention further proposes a circular microwave ablation system, characterized by using the above-mentioned circular microwave ablation antenna with a special structure.

BRIEF DESCRIPTION OF THE DRAWINGS

The present invention will be further described with reference to the accompanying drawings.

Figure 1:
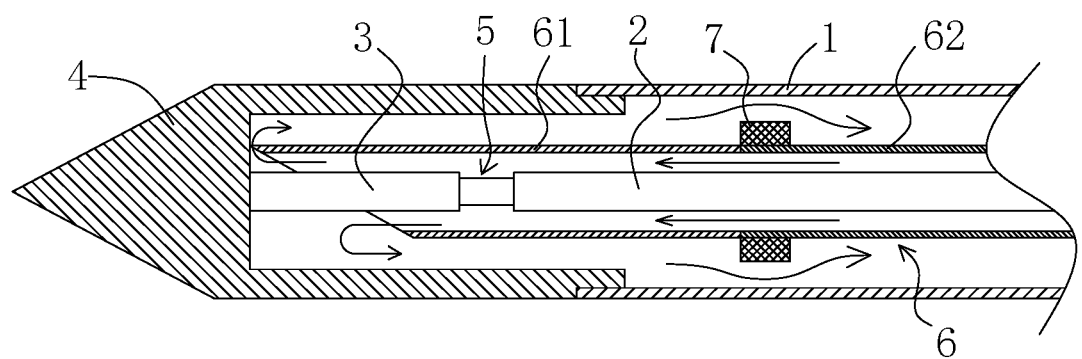
FIG. 1 is a cross-sectional view of a front end portion of a circular microwave ablation antenna of Embodiment 1.

In the drawings: 1—needle bar, 2—coaxial cable, 3—pole core, 4—needle head, 5—antenna emission window, 6—conduit, 61—first sub-conduit, 62—second sub-conduit, 7—choke ring, 8—medium casing, 9—protrusion.

DETAILED DESCRIPTION OF THE EMBODIMENTS

In order to make the objectives, the technical solutions and advantages of the embodiments of the present invention more clear, the technical solutions of the embodiments of the present invention will be described clearly and completely with reference to the accompanying drawings in the embodiments of the present invention.

Embodiment 1

As shown in FIG. 1, a circular microwave ablation antenna provided by the present invention includes a needle head 4, a needle bar 1, a coaxial cable 2, a conduit 6 and a choke ring 7. The antenna is provided with a chamber for accommodating coaxial cable 2 and conduit 6, and a water inlet channel is disposed between conduit 6 and coaxial cable 2 (a gap between conduit 6 and coaxial cable 2 is suggested as a water inlet channel), and a water return channel is disposed between the conduit 6 and the needle bar 1 (a gap between conduit 6 and needle bar 1 is suggested as a water return channel). As shown in FIG. 1, needle head 4 (zirconium dioxide head) is provided with a blind hole having an opening facing backward, and a pole core 3 is arranged in the blind hole. The inner conductor of coaxial cable 2 is connected to pole core 3 (electrical connection), an antenna emission window 5 is formed between pole core 3 and the outer conductor of coaxial cable 2. A chamber is formed between the wall of the blind hole and pole core 3 and the outer conductor of coaxial cable 2, and the front end of the conduit is close to or abuts against the bottom of the blind hole, so that antenna emission window 5 (at least partially) is located in the conduit, thereby the cooling medium can cool the emission window area of the antenna. In this embodiment, the cooling medium is drained to the most front end of the antenna through the conduit, thus the central region of the microwave radiation can be cooled.

As shown in FIG. 1, in the present embodiment, conduit 6 is provided with a first sub-conduit 61 close to the needle head and a second sub-conduit 62 away from the needle head. First sub-conduit 61 is made of insulation material, which can be selected from polyvinyl chloride (PVC), or polytetrafluoroethylene (PTFE) or the like, so that the microwave can radiate outward, and the rear portion thereof is hermetically connected to second sub-conduit 62 to ensure the cooling medium is transported forward; second sub-conduit 62 is made of metal material, which can be selected from copper or stainless steel, the front portion thereof is hermetically fixed to choke ring 71 by welding, so that the choke ring acts to block the microwave. A gap exists between the choke ring and the needle bar, and the gap is used for the backflow of the cooling medium. In FIG. 1, the arrows in the antenna chamber represent the flow direction of the cooling medium.

In this embodiment, first sub-conduit 61 and second sub-conduit 62 of conduit 6 are hermetically butted, and choke ring 7 is sleeved outside second sub-conduit 62 and hermetically fixed by welding. The conduit and the choke ring can also use other assembly structures, for example:

1. First sub-conduit 61 and second sub-conduit 62 are respectively fixed to the front end and rear end of choke ring 7.

2. First sub-conduit is inserted into the inner hole of choke ring 7 for hermetical fixing; second sub-conduit 62 is hermetically welded to the rear end of choke ring 7.

3. Choke ring 7 is sleeved outside second sub-conduit 62, and first sub-conduit 61 is inserted into the front portion of second sub-conduit 62.

The use of the above assembly structures falls within the protection scope of the present invention.

Embodiment 2

Figure 2:
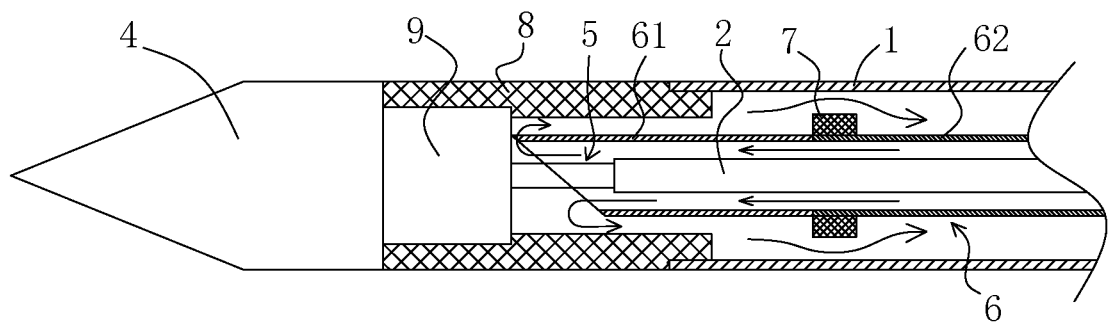
FIG. 2 is a cross-sectional view of a front end portion of a circular microwave ablation antenna of Embodiment 2.

As shown in FIG. 2, the main structure of the embodiment is basically the same as that of Embodiment 1, the difference is the front-end portion of the antenna. In this embodiment, needle head 4 is a metal head, the tail of the metal head is provided with a rearward protrusion 9, and the inner conductor of coaxial cable 2 is connected to the tail (protrusion 9) of the metal head, an antenna emission window 5 is formed between the rear end of the metal head (protrusion 9) and the front end of the outer conductor of coaxial cable 2. Needle head 4 is connected to needle bar 1 through medium casing 8, and a chamber is formed between medium casing 8 and coaxial cable 2. The conduit extends forward into the chamber, and the antenna emission window is at least partially located in the conduit, so that the cooling medium is capable of cooling the emission window area of the antenna.

Another variation is as follows: the metal head is directly connected to the needle bar, and a chamber is formed between the front end of the needle bar and the coaxial cable, and the conduit extends forward into the chamber, so that the antenna emission window is at least partially located in the conduit.

In addition, the present invention further provides a circular microwave ablation system including the aforementioned circular microwave ablation antenna. The present invention also protects the aforementioned circular microwave ablation antenna used for a circular microwave ablation system.

In addition to the above-mentioned embodiments, the present invention may have other modes of implementation. Any technical solutions formed by equivalent replacement or equivalent transformation fall within the protection scope of the present invention.

What is claimed is:

1. A circular microwave ablation antenna, comprising a needle head, a needle bar, a coaxial cable, a conduit, and a choke ring; wherein the circular microwave ablation antenna is provided with a chamber, the chamber accommodates the coaxial cable and the conduit, a water inlet channel is disposed between the conduit and the coaxial cable, and a water return channel is disposed between the conduit and the needle bar; the chamber and the conduit extend forward to a front end of the circular microwave ablation antenna, and an antenna emission window is located in the conduit to enable a cooling medium to cool an area of the antenna emission window; a part of the conduit in a microwave emission area is made of a microwave permeable material, so that a microwave radiates outward, and the rest of the conduit is made of a microwave shielding material; the choke ring is located at a rear side of the microwave emission area and is hermetically fixed to the conduit, so that the choke ring blocks the microwave, a gap is provided between the choke ring and the needle bar for a backflow of the cooling medium, wherein the needle head is a metal head, a tail of the metal head protrudes backward, and an inner conductor of the coaxial cable is connected to the tail of the metal head; the antenna emission window is formed between a rear end of the metal head and a front end of an outer conductor of the coaxial cable; and wherein the choke ring is directly contacting an external wall of the conduit in a region between the conduit and the needle head.

2. The circular microwave ablation antenna of claim 1, wherein the needle head is provided with a blind hole, and a pole core is arranged in the blind hole, an inner conductor of the coaxial cable is connected to the pole core, the antenna emission window is formed between the pole core and an outer conductor of the coaxial cable, and a front end of the conduit abuts against a bottom of the blind hole.

3. The circular microwave ablation antenna of claim 1, wherein the metal head is connected to the needle bar through a medium casing, the chamber is formed between the medium casing and the coaxial cable, and the conduit extends forward into the chamber.

4. The circular microwave ablation antenna of claim 1, wherein the metal head is connected to the needle bar, the chamber is formed between a front end of the needle bar and the coaxial cable, and the conduit extends forward into the chamber.

5. The circular microwave ablation antenna of claim 1, wherein the choke ring is sleeved outside the conduit.

6. The circular microwave ablation antenna of claim 1, wherein the conduit is provided with a first sub-conduit and a second sub-conduit, the first sub-conduit is close to the needle head as compared to the second sub-conduit, the first sub-conduit is made of an insulation material, a rear portion of the first sub-conduit is hermetically connected to the second sub-conduit or the choke ring; the second sub-conduit is made of a metal material, a front portion of the second sub-conduit is hermetically fixed to the choke ring through a welding.

7. A circular microwave ablation system, comprising a circular microwave ablation antenna, wherein the circular microwave ablation antenna comprises a needle head, a needle bar, a coaxial cable, a conduit, and a choke ring; the circular microwave ablation antenna is provided with a chamber, the chamber accommodates the coaxial cable and the conduit, a water inlet channel is disposed between the conduit and the coaxial cable, and a water return channel is disposed between the conduit and the needle bar; the chamber and the conduit extend forward to a front end of the circular microwave ablation antenna, and an antenna emission window is located in the conduit to enable a cooling medium to cool an area of the antenna emission window; a part of the conduit in a microwave emission area is made of a microwave permeable material, so that a microwave radiates outward, and the rest of the conduit is made of a microwave shielding material; the choke ring is located at a rear side of the microwave emission area and is hermetically fixed to the conduit, so that the choke ring blocks the microwave, a gap is provided between the choke ring and the needle bar for a backflow of the cooling medium, wherein the needle head is a metal head, a tail of the metal head protrudes backward, and an inner conductor of the coaxial cable is connected to the tail of the metal head; the antenna emission window is formed between a rear end of the metal head and a front end of an outer conductor of the coaxial cable; and wherein the choke ring is directly contacting an external wall of the conduit in a region between the conduit and the needle head.

8. The circular microwave ablation system of claim 7, wherein the needle head is provided with a blind hole, and a pole core is arranged in the blind hole, an inner conductor of the coaxial cable is connected to the pole core, the antenna emission window is formed between the pole core and an outer conductor of the coaxial cable, and a front end of the conduit abuts against a bottom of the blind hole.

9. The circular microwave ablation system of claim 7, wherein the metal head is connected to the needle bar through a medium casing, the chamber is formed between the medium casing and the coaxial cable, and the conduit extends forward into the chamber.

10. The circular microwave ablation system of claim 7, wherein the metal head is connected to the needle bar, the chamber is formed between a front end of the needle bar and the coaxial cable, and the conduit extends forward into the chamber.

11. The circular microwave ablation system of claim 7, wherein the choke ring is sleeved outside the conduit.

12. The circular microwave ablation system of claim 7, wherein the conduit is provided with a first sub-conduit and a second sub-conduit, the first sub-conduit is close to the needle head as compared to the second sub-conduit, the first sub-conduit is made of an insulation material, a rear portion of the first sub-conduit is hermetically connected to the second sub-conduit or the choke ring; the second sub-conduit is made of a metal material, a front portion of the second sub-conduit is hermetically fixed to the choke ring through a welding.

* * * * *